United States Patent [19]

Sunohara et al.

[11] Patent Number: 5,478,570
[45] Date of Patent: Dec. 26, 1995

[54] PROCESS FOR PRODUCING CAPSULE AND CAPSULE OBTAINED THEREBY

[75] Inventors: Hideki Sunohara; Tohru Ohno; Nobuyuki Shibata; Keisuke Seki, all of Osaka, Japan

[73] Assignee: Morishita Jintan Co., Ltd., Osaka, Japan

[21] Appl. No.: 271,446

[22] Filed: Jul. 7, 1994

[30] Foreign Application Priority Data

Jul. 8, 1993 [JP] Japan ................ 5-168891

[51] Int. Cl.⁶ .................. A61K 9/48; A61K 35/74
[52] U.S. Cl. .......... 424/463; 424/451; 424/455; 424/490; 424/93.48
[58] Field of Search ............ 424/451, 463, 424/490, 455

[56] References Cited

FOREIGN PATENT DOCUMENTS

| | | |
|---|---|---|
| 0525731A2 | 2/1993 | European Pat. Off. . |
| 61-151127 | 7/1986 | Japan . |
| 62-201823 | 2/1988 | Japan . |

*Primary Examiner*—Thurman K. Page
*Assistant Examiner*—James M. Spear
*Attorney, Agent, or Firm*—Foley & Lardner

[57] ABSTRACT

The present invention provides a process for producing a capsule containing a substance which is liable to acid, water or heat, comprising: suspending a substance which is liable to acid, water or heat in a hydrophobic substance which is non-flowable at ambient temperature; encapsulating the resulting suspension; air-drying the resulting capsule at ambient temperature; and vacuum drying or vacuum freeze-drying the air-dried capsule. A capsule obtained by the process is also disclosed.

3 Claims, No Drawings

PROCESS FOR PRODUCING CAPSULE AND CAPSULE OBTAINED THEREBY

FIELD OF THE INVENTION

The present invention relates to a process for producing a capsule capable of protecting a content from acid, water or heat, and a capsule obtained thereby.

BACKGROUND OF THE INVENTION

Useful enterobacteria are liable to acid, water or heat, and when they are directly incorporated in the body without any protective means, almost all of them are killed. However, by protecting the useful enterobacteria from acid, water or heat with an enteric capsule, a surviving rate thereof can be increased.

For example, such a capsule containing the useful enterobacteria is disclosed in Japanese Laid-Open Patent Publication No. 61-151127. In Japanese Laid-Open Patent Publication No. 61-151127, there is described a method for producing an enteric capsule comprising: mixing bacteria cells with vehicles such as starch; dispersing the resulting mixture in a hardening oil; encapsulating the resulting dispersion with an enteric coating consisting of gelatin and pectin; and then dipping the resulting capsule in an aqueous calcium chloride solution to impart acid resistance to the capsule. In the capsule obtained by this method, intrusion of water into a content dispersed in the hardening oil can be interfered temporarily by the hardening oil, however, bad influence with time caused by residual water which is contained in a coating of the capsule and the hardening oil can not be avoided. In addition, in order to impart acid resistance to a coating of the capsule consisting of gelatin/pectin, the capsule must be dipped in an aqueous calcium chloride solution. At this step, water is liable to transfer to a content through a coating of the capsule, as well as heat resistance of the resulting capsule is poor.

On the other hand, in Japanese Laid-Open Patent Publication No. 62-263128, there is described a capsule wherein the useful enterobacteria are isolated from a coating of the capsule via a hydrophobic substance which is non-flowable at ambient temperature. In this structure, penetration of water into the content can also be interfered temporarily, however, bad influence with time caused by residual water which is contained in a coating of the capsule, the hardening oil and other substance, can not be avoided, as well as heat resistance of the resulting capsule is poor.

SUMMARY OF THE INVENTION

An object of the present invention is to provide a process for producing a capsule containing a substance which is liable to acid, water or heat, comprising: suspending a substance which is liable to acid, water or heat in a hydrophobic substance which is non-flowable at ambient temperature; encapsulating the resulting suspension; air-drying the resulting capsule at ambient temperature; and vacuum drying or vacuum freeze-drying the air-dried capsule.

Another object of the present invention is to provide a capsule capable of protecting the content from acid, water or heat, which is obtained by the above process.

These as well as other objects and advantages of the present invention will become apparent to those skilled in the art from the following description.

DETAILED DESCRIPTION OF THE INVENTION

The present invention provides a process for producing a capsule containing a substance which is liable to acid, water or heat, comprising: suspending a substance which is liable to acid, water or heat in a hydrophobic substance which is non-flowable at ambient temperature; encapsulating the resulting suspension; air-drying the resulting capsule at ambient temperature; and vacuum drying or vacuum freeze-drying the air-dried capsule.

The present invention also provides a capsule encapsulating a suspension prepared by suspending a substance which is liable to acid, water or heat in a hydrophobic substance which is non-flowable at ambient temperature, by the use of a coating mainly composed of gelatin, wherein said capsule has an Aw value of not more than 0.20 and a thermal conductivity of not more than 0.16 Kcal/mh°C.

The content used for the capsule of the present invention may be anyone which is liable to acid, water or heat, but preferably useful enterobacteria. Examples of the useful enterobacteria include Bifidobacterium, *Enterococcus faecalis*, *Lactobacillus acidophilus* and the like.

In the present invention, it is necessary to suspend the above content in a hydrophobic substance which is non-flowable at ambient temperature, firstly. The reason for suspending the content in the hydrophobic substance is to prevent that the content suffers a bad influence from a lot of water present in the course of producing the capsule. Examples of the hydrophobic substance include edible hardening fats and fatty oils, sucrose fatty acid esters (SAIB), glycerin fatty acid esters and the like. Particularly preferred hydrophobic substance is a hardening coconut oil (WITOCAN-H, WITOCAN-42/44, manufactured by Huels Co.).

It is necessary to encapsulate a suspension of the content into the hydrophobic substance with an enteric coating. The encapsulation method is not specifically limited, but example of the most preferable method include a so-called "dropping method". The method includes dropping a core substance in a solidifying solution using a twofold or threefold nozzle (e.g. Japanese Laid-Open Patent Publication Nos. 49-59789, 51-8176 and 60-172343, etc.). Further, the capsule can also be obtained by molding the content of the capsule by using a capsule coating substance separated into two upper/lower pieces.

In producing the capsule of the present invention, when using a threefold nozzle-dropping method, the content is discharged through a most-inner nozzle and a coating is discharged through a most-outer nozzle. It is preferred that the hardening fats and fatty oils used in Japanese Laid-Open Patent Publication No. 60-172343 described above in the "BACKGROUND OF THE INVENTION" is discharged through an intermediate nozzle. In this case, the resulting capsule has a three-layered structure and a substance which is liable to acid, water or heat is contained in the most-inner part thereof. It is considered that this is the most excellent embodiment of the present invention because the amount of water intrude into the capsule from the outside is extremely little.

In general, the enteric coating is mainly composed of gelatin and pectin. Various substances can be contained in the enteric coating and, further, oligosaccharide and glycerin can be formulated in order to increase water activity of the coating. The weight ratio of gelatin to pectin is 70:30 to 95:5, preferably 80:20 to 90:10. When oligosaccharide is formulated, the amount is 2 to 20 parts by weight, preferably 5 to 10 parts by weight, based on the total weight of gelatin and pectin. Further, when glycerin is formulated, the amount is 5 to 80 parts by weight, preferably 40 to 70 parts by weight, based on 100 parts by weight of gelatin and pectin.

The capsule thus obtained is air-dried at ambient temperature. It is usual to use a method of drying in air at 5° to 30° C. The drying time is suitably 2 to 12 hours.

It is outstanding characteristic of the present invention to subject the capsule dried by a conventional method to an additional vacuum drying or vacuum freeze-drying. The vacuum degree during the process is maintained at 0.5 to 0.02 torr, and the freezing temperature is employed of not more than −20° C. in the case of vacuum freeze-drying. The time required for vacuum drying or vacuum freeze-drying is not specifically limited, but it is normally 5 to 60 hours, preferably 24 to 48 hours. When the time is shorter than 5 hours, the drying becomes insufficient and, therefore, the content may have a bad influence from water present in the capsule.

Regarding the capsule obtained by the process of the present invention, water in the capsule is completely removed by vacuum freeze-drying, and an Aw value is not more than 0.20 and thermal conductivity is not more than 0.16 Kcal/mh°C. Since the amount of water is decreased by vacuum drying or vacuum freeze-drying and, at the same time, the capsule is completely dried to become porous, the thermal conductivity is extremely decreased in comparison with those obtained by only dried under ambient environment. Further, it has been found in the present invention that the enteric coating can be obtained even if the coating of the mixture of gelatin and pectin is not treated with an aqueous calcium chloride solution. As described above, by providing enteric coating, the content can effectively reach the intestines without being killed by gastric acid when the content is incorporated in the human body.

The Aw value does not mean an absolute amount of water, but a value determined by the present state of water, that is, a degree of freedom of water contained in a sample, which is an index representing water which can be concerned directly with the chemical reaction or growth of microorganism and is measured by an electric resistance type water activity measuring method (Aw meter WA-360, manufactured by Shibaura Denshi Seisakusho Co., Ltd.). The thermal conductivity is measured by a Fitch method. The Aw value is preferably not more than 0.20 and the thermal conductivity is preferably 0.08 to 0.02 Kcal/mh°C. The size of the capsule is not specifically limited, but the diameter is normally 0.3 to 8 mm, preferably 1 to 3 mm.

According to the above means, since the water activity value of the whole capsule is lowered, an influence of water with time on the content can be prevented. Further, since thermal conductivity is also decreased, thermal insulation properties is enhanced. In case of vacuum freeze-drying, since water in the capsule is sublimated, it becomes porous, which results in enhancement of thermal insulation properties. Furthermore, when acid resistance is imparted to the gelatin/pectin coating, since it is gelated to produce the enteric coating by selecting pectin without dipping in the calcium chloride solution, no water is transferred from the coating to the content and a secondary treatment can be eliminated.

The capsule of the present invention has passed an enteric test based on a disintegration test of Japanese Pharmacopoeia and it has been confirmed that the capsule does not dissolve in the stomach, but dissolves in the intestines.

Accordingly, by incorporating the groups of Bifidobacterium as anaerobic bacteria which is liable to acid, water or heat in the above capsule, a large amount of Bifidobacterium can reach the intestines and, at the same time, decrease of the viable microbe cell number can be prevented during storage for a long period of time.

The following Examples and Comparative Examples further illustrate the present invention in detail but are not to be construed to limit the scope thereof.

EXAMPLES

Example 1

Commercially available microbe cell powder (viable microbe cell number of Lactobacillus bifidus: 6×10 10/g), which was prepared by mixing original microbe cells of *Bifidobacterium longum* with a vehicle and then freeze-drying, and oligosaccharide were dispersed in molten hardening fats and fatty oils having a melting point of 34° C. The resulting suspension, a molten solution of a hardening oil having a melting point of 43° C. and a gelatin/pectin solution which forms a coating were simultaneously dropped in a cold flowing oil through an core nozzle of a concentric threefold nozzle, an intermediate shell nozzle provided outside of the core nozzle, and an outer shell nozzle, respectively, to produce a three-layered seamless capsule having a diameter of 2.5 mm.

After the completion of air-drying under ambient environment, the capsule was vacuum dried or vacuum freeze-dried to decrease water activity of the capsule until the capsule has an Aw value of not more than 0.20 and a thermal conductivity of not more than 0.16 Kcal/mh°C., respectively.

Comparative Example 1

According to the same manner as that described in Example 1 except that being omitted the step of vacuum freeze-drying, a seamless capsule was produced.

Storage test

The capsules obtained in Example 1 and Comparative Example 1 were stored at 20° C. and 37° C., respectively, to examine stability thereof.

As a result, a relation between a storage period (days) and a viable microbe cell number of *Bifidobacterium longum* is as shown in Tables 1 and 2, below.

TABLE 1

| | Storage temperature: 20° C. | |
|---|---|---|
| | Example | Comparative Example |
| Initial | $1.4 \times 10^9$ | $1.7 \times 10^9$ |
| After 1 month | $1.2 \times 10^9$ | $4.0 \times 10^8$ |
| After 2 months | $1.1 \times 10^9$ | $3.2 \times 10^8$ |
| After 4 months | $1.2 \times 10^9$ | $2.4 \times 10^8$ |
| After 6 months | $1.1 \times 10^9$ | $1.2 \times 10^7$ |

[viable microbe cell number/g capsule]

TABLE 2

| | Storage temperature: 37° C. | |
|---|---|---|
| | Example | Comparative Example |
| Initial | $1.4 \times 10^9$ | $1.7 \times 10^9$ |
| After 1 month | $1.0 \times 10^9$ | $2.6 \times 10^8$ |

TABLE 2-continued

| Storage temperature: 37° C. | | |
| --- | --- | --- |
| | Example | Comparative Example |
| After 2 months | $8.5 \times 10^8$ | $1.3 \times 10^8$ |
| After 4 months | $5.1 \times 10^8$ | $7.8 \times 10^7$ |
| After 6 months | $3.2 \times 10^8$ | $9.2 \times 10^6$ |

[viable microbe cell number/g capsule]

What is claimed is:

1. A process for producing a capsule containing Bifidobacterium, comprising: suspending Bifidobacterium in an edible fat which is non-flowable at ambient temperature; encapsulating the resulting suspension; air-drying the resulting capsule at ambient temperature; and vacuum drying or vacuum freeze-drying the air-dried capsule.

2. A capsule prepared by encapsulating a substance which is liable to acid, water or heat suspended in an edible hardening fat which is non-flowable at ambient temperature, by the use of a coating mainly composed of gelatin, wherein the capsule has an Aw value of not more than 0.20 and a thermal conductivity of not more than 0.16 Kcal/mh°C., and wherein the substance which is liable to acid, water or heat is useful enterobacteria.

3. The capsule according to claim 2, wherein the useful enterobacteria are Bifidobacterium.

* * * * *